US012714464B2

(12) United States Patent
Rich et al.

(10) Patent No.: US 12,714,464 B2
(45) Date of Patent: Aug. 25, 2026

(54) METHOD AND SYSTEM FOR INSUFFLATING A BODY CAVITY USING A PERCUTANEOUS NEEDLE

(71) Applicant: Lexion Medical, LLC, St. Paul, MN (US)

(72) Inventors: Brian Rich, Blaine, MN (US); Carl M. Geisz, Edina, MN (US)

(73) Assignee: Lexion Medical, LLC, St. Paul, MN (US)

( * ) Notice: Subject to any disclaimer, the term of this patent is extended or adjusted under 35 U.S.C. 154(b) by 580 days.

(21) Appl. No.: 18/337,849

(22) Filed: Jun. 20, 2023

(65) Prior Publication Data

US 2024/0423667 A1 Dec. 26, 2024

(51) Int. Cl.

*A61B 17/34* (2006.01)
*A61M 13/00* (2006.01)
*A61M 16/00* (2006.01)

(52) U.S. Cl.

CPC ....... *A61B 17/3474* (2013.01); *A61B 17/3417* (2013.01); *A61B 17/3462* (2013.01); *A61M 13/006* (2014.02); *A61M 16/0003* (2014.02); *A61M 2016/0027* (2013.01); *A61M 2205/3337* (2013.01); *A61M 2205/3344* (2013.01)

(58) Field of Classification Search

CPC ............ A61B 17/3474; A61B 17/3417; A61B 17/3462; A61M 13/006; A61M 16/0003; A61M 2016/0027; A61M 2205/3337; A61M 2205/3344

See application file for complete search history.

(56) References Cited

U.S. PATENT DOCUMENTS

| | | | | |
|---|---|---|---|---|
| 2002/0183715 A1 | 12/2002 | Mantell et al. | | |
| 2010/0198149 A1* | 8/2010 | Fox .................... | A61B 17/3478 604/99.01 | |
| 2017/0274160 A1 | 9/2017 | Mantell et al. | | |
| 2021/0267639 A1* | 9/2021 | Fischer .............. | A61B 17/3462 | |
| 2021/0322684 A1 | 10/2021 | Fischer et al. | | |
| 2022/0168512 A1 | 6/2022 | Teh et al. | | |

OTHER PUBLICATIONS

Patent Cooperation Treaty; PCT: Notification of transmittal of the international search report and the written opinion of the international searching authority, or the declaration; International Appln No. PCT/US2024/033516; date of mailing: Sep. 16, 2024.

* cited by examiner

*Primary Examiner* — Dung T Ulsh
(74) *Attorney, Agent, or Firm* — Baker Botts L.L.P.

(57) ABSTRACT

An insufflation needle includes a hub portion and a shaft portion. The shaft portion extends at least partially into the hub portion and includes an outer lumen and at least one inner lumen. The outer lumen has a diameter between approximately 3.0 mm and 5.0 mm and includes at least one aperture at a first end of the outer lumen, which is positioned proximal to the hub portion of the needle, and at least one aperture at a second end of the outer lumen, which terminates in a needle point. The at least one inner lumen has a diameter between approximately 0.8 mm and 2 mm.

18 Claims, 3 Drawing Sheets

METHOD AND SYSTEM FOR INSUFFLATING A BODY CAVITY USING A PERCUTANEOUS NEEDLE

TECHNICAL FIELD

The present disclosure relates generally to medical procedures and more particularly to a method and system for insufflating a body cavity using a percutaneous needle.

BACKGROUND

Providing an insufflation fluid into a body cavity is referred to as insufflation. The purpose of insufflation is to inflate or distend the body cavity to allow a surgeon to explore a surgical site and/or otherwise provide a view of the site to be treated or observed. Insufflation is used in many common procedures including endoscopic surgical procedures, laparoscopic procedures performed on the abdominal cavity and orthoscopic procedures performed on the chest cavity.

As will be recognized by one of ordinary skill in the art, insufflation of a body cavity may be performed in phases or stages, beginning with an initial insufflation stage and proceeding to one or more supplemental insufflation stages. See U.S. application Ser. No. 16/407,814, which issued as U.S. Pat. No. 11,541,191 and is incorporated by reference herein. The staging or phasing of insufflation may provide various benefits to the patient.

Phased insufflation may begin in a first phase, where insufflation fluid is delivered to the body cavity via a small profile medical appliance, such as a veress needle. A veress needle is typically used for initial insufflation to create pneumoperitoneum before a larger profile medical appliance, such as a trocar, can safely enter the body cavity and provide insufflation to the body cavity for the remainder of a surgery. One benefit of using a veress needle for the initial stage of insufflation is that the small size of the needle reduces the likelihood of piercing or otherwise puncturing an organ relative to the risk posed by a larger medical access appliance.

SUMMARY OF THE INVENTION

According to one embodiment, a system includes an insufflator and a needle. The insufflator is coupled to the needle and is configured to supply insufflation fluid. The needle is configured to facilitate the delivery of the insufflation fluid to a body cavity. The needle includes a shaft portion extending at least partially into a hub portion. The shaft portion includes an outer lumen having a diameter between approximately 3.0 mm and 5.0 mm and a wall thickness between approximately 0.006 inches and 0.010 inches. The outer lumen further includes at least one aperture at a first end of the outer lumen and at least one aperture at a second end of the outer lumen, wherein the first end is positioned proximal to the hub portion of the needle and the second end terminates in a needle point. The shaft portion also includes an inner lumen having a diameter between approximately 0.8 mm and 1.3 mm.

According to another embodiment, a method includes insufflating a body cavity with a system comprising an insufflator and a needle. The insufflator is coupled to the needle, and is configured to supply insufflation fluid. The needle is configured to facilitate the delivery of the insufflation fluid to a body cavity. The needle includes a shaft portion extending at least partially into a hub portion. The shaft portion includes an outer lumen having a diameter between approximately 3.0 mm and 5.0 mm and a wall thickness between approximately 0.006 inches and 0.010 inches. The outer lumen further includes at least one aperture at a first end of the outer lumen and at least one aperture at a second end of the outer lumen, wherein the first end is positioned proximal to the hub portion of the needle and the second end terminates in a needle point. The shaft portion also includes an inner lumen having a diameter between approximately 0.8 mm and 1.3 mm and a wall thickness between approximately 0.004 inches and 0.008 inches.

According to yet another embodiment, an insufflation needle comprises a needle coupled to an insufflator and configured to facilitate delivery of insufflation fluid to a body cavity. The needle includes a shaft portion extending at least partially into a hub portion. The shaft portion includes an outer lumen having a diameter between approximately 3.0 mm and 5.0 mm and a wall thickness between approximately 0.006 inches and 0.010 inches. The outer lumen further includes at least one aperture at a first end of the outer lumen and at least one aperture at a second end of the outer lumen, wherein the first end is positioned proximal to the hub portion of the needle and the second end terminates in a needle point. The shaft portion also includes an inner lumen having a diameter between approximately 0.8 mm and 1.3 mm and a wall thickness between approximately 0.004 inches and 0.008 inches.

The teachings of the disclosure provide one or more technical advantages. Embodiments of the disclosure may have none, some, or all of these advantages. For example, in some embodiments, the systems and methods described herein enable insufflation via a percutaneous needle for the entire duration of a medical procedure. In particular, certain embodiments of the invention disclosed herein exhibit properties and/or attributes that permit insufflation fluid to be delivered to a body cavity at rates necessary to sufficiently insufflate a body cavity for the entirety of a medical procedure (i.e., from beginning to end). Accordingly, the inventions disclosed herein may eliminate or otherwise reduce the need for staged or phased insufflation (i.e., providing, in a first phase, insufflation via a first medical appliance (e.g., veress needle) and subsequently providing, in a second phase, insufflation via a supplemental medical appliance (e.g., trocar)). By implementing the systems and methods provided herein, patient risks associated with insufflation may be reduced, making insufflation safer and less invasive, and/or causing less discomfort for patients undergoing a medical procedure. For example, reducing or eliminating the need for supplemental insufflation appliances may result in a reduced risk of organ puncture and/or a reduced likelihood of insufflation fluid leakage leading to deflation of the body cavity. Such risks are recognized and described in further detail in U.S. Pat. No. 11,541,191.

As another example, the systems and methods described herein may reduce the complexity and duration of insufflation given that the insufflation needle described herein may be positioned in any spot deemed acceptable by a physician or other medical professional, without continuous visualization during the surgical procedure and/or without the need to consider surgical instrument obstruction or triangulation.

As yet another example, the systems and methods described herein may reduce or eliminate the need for suture at the close of surgery at least in part due to the unique properties and/or attributes of the claimed invention. This may present other advantages such as quicker recovery, diminished chances for scarring or other lasting skin imperfections, and other surgical complications (e.g., infection at the incision site). Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE DRAWINGS

Figure 1A:
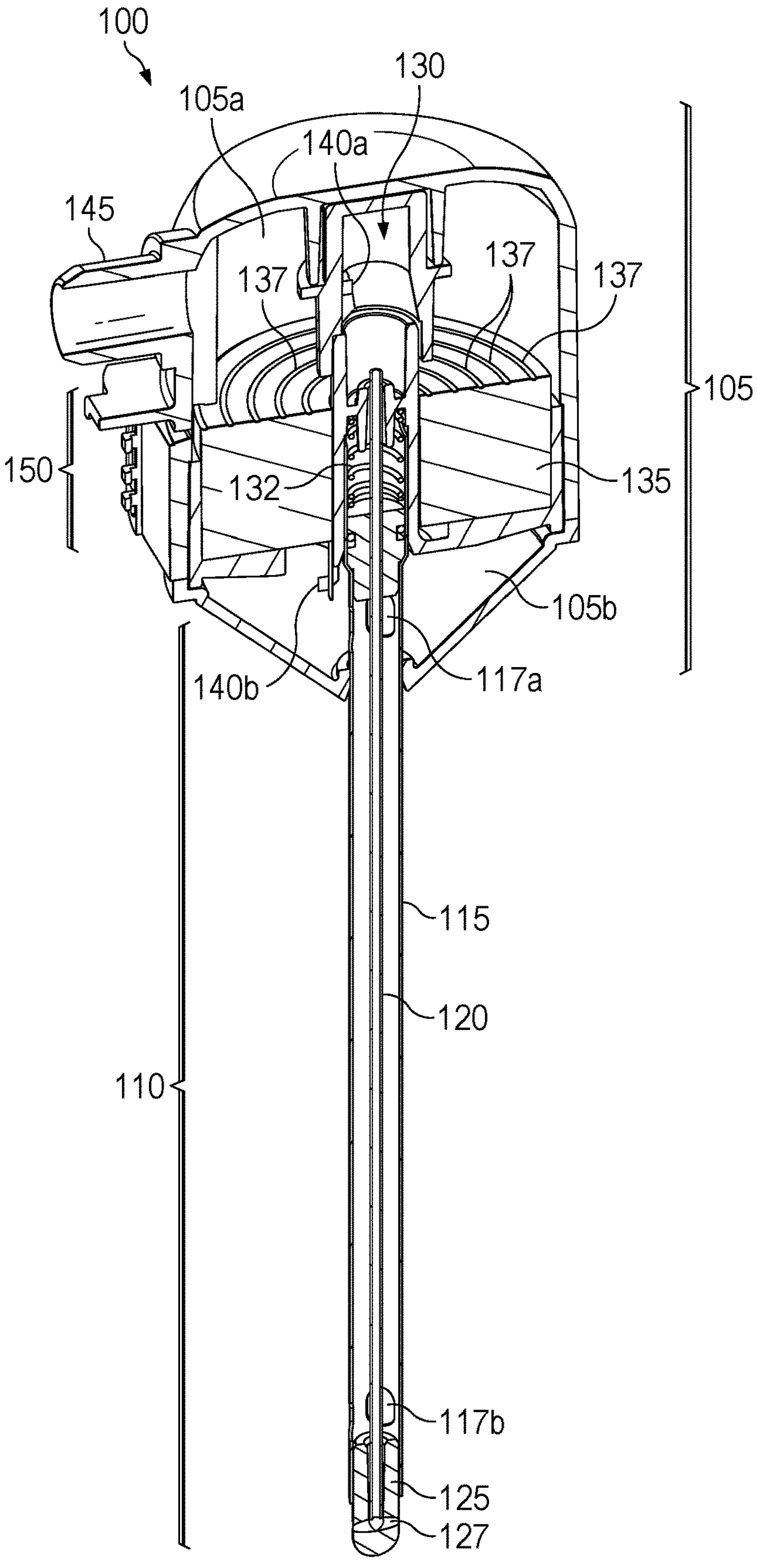
FIG. 1A illustrates an example of a cross section of an insufflation needle, according to certain embodiments of the present invention.

One of the requirements for delivery of insufflation fluid to a patient's body cavity is to maintain the proper flow of insufflation fluid into the body cavity. Normally, fluid flows from a high-pressure fluid source, which is remote from the patient, through one or more medical access appliances before being injected into the patient's body cavity. Typically, the insufflation fluid is stored in high-pressure containers and a pressure regulator reduces the pressure of the fluid to a lower pressure. The low pressure fluid is typically delivered to the body cavity through at least one medical access appliances containing a set of inline end connectors that couple the source of insufflation fluid, the pressure regulator, the filter, the heater, the hydrator, and the appliance(s) to each other. Typically, before being delivered to the body cavity, the insufflation fluid is conditioned by filtering, heating and/or hydrating. The insufflation fluid may flow through any suitable number of inline end connectors, which are typically connected by flexible tubing (also referred to herein as conduits), before being delivered to the body cavity.

As described above and in U.S. Pat. No. 11,541,191, a veress needle is conventionally used during a first phase of insufflation. The veress needle is inserted percutaneously into a patient at the start of a medical procedure and provides initial insufflation to a body cavity. Once pneumoperitoneum is achieved via the initial stage of insufflation, a larger medical access appliance (e.g., a trocar) is able to be inserted into the body cavity and facilitates insufflation for the remainder of the medical procedure. As will be recognized by one of ordinary skill in the art, a larger medical access device is used to provide insufflation for the remaining duration of surgery because conventional veress needles are unable to deliver insufflation fluid to the body cavity at rates necessary to maintain the pneumoperitoneum required during surgery due at least in part to the small size of the veress needle.

In particular, the diameter of a conventional veress needle measures between 2.1-3.5 mm. The dimensioning of the needle is beneficial in that it is small enough that it typically does not leave a patient with any scarring or lasting skin imperfections that would otherwise result from suturing an insufflation access point but is large enough to create a pneumoperitoneum necessary to safely insert a larger medical access appliance to provide insufflation for the duration of a surgery. Importantly, the dimensioning of conventional veress needles only support insufflation flow rates of up to 8 liters per minute, which is insufficient to maintain pneumoperitoneum during surgery. It is for this reason that physicians or other medical practitioners must insert and use a larger medical access appliance, such as a trocar, to deliver insufflation fluid to the body cavity during surgery. These larger appliances are capable of maintaining pneumoperitoneum during surgery because they are configured to deliver insufflation fluid at flow rates exceeding 10 liters per minute.

As one of ordinary skill in the art will recognize, conventional two-phase insufflation solutions like the one described above face leakage risk due to disconnection and reconnection of interconnecting components, such as conduit(s) connecting the veress needle and/or trocar to the insufflator. Once the body cavity is sufficiently insufflated using the veress needle, the conduit is disconnected from the veress needle and connected to the trocar). But this disconnection and reconnection of the conduit to the veress needle and, subsequently, the trocar presents an opportunity for insufflation fluid leakage and therefore poses an increased safety risk to the patient due to the possible deflation of the body cavity and threat of piercing or puncturing an organ.

The present disclosure describes an insufflation system and method that overcomes the shortcomings of the conventional insufflation solutions described above. In particular, the present disclosure describes an insufflation system and method that eliminates the insufflation phasing or staging discussed above, thereby also reducing or eliminating associated risks of phased/staged insufflation. Notably, embodiments of the present invention include an insufflation needle capable of delivering insufflation fluid to the body cavity at flow rates necessary to maintain pneumoperitoneum for the entire duration of surgery. Example embodiments are best understood by referring to FIGS. 1A through 2 of the drawings and the description below, like numerals being used for like and corresponding parts of the various drawings.

Figure 1B:
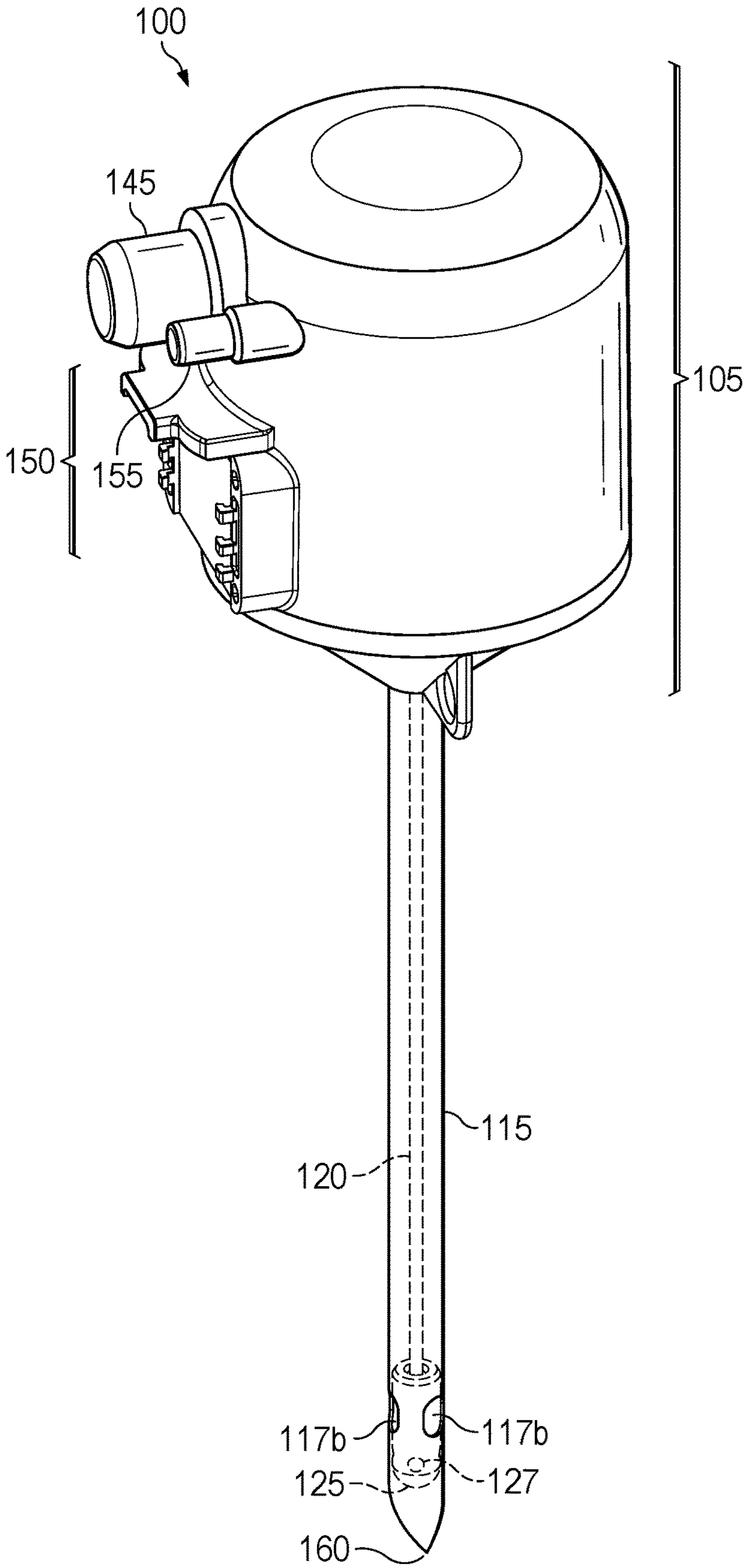
FIG. 1B illustrates a perspective view of the insufflation needle depicted in FIG. 1A.
Figure 2:
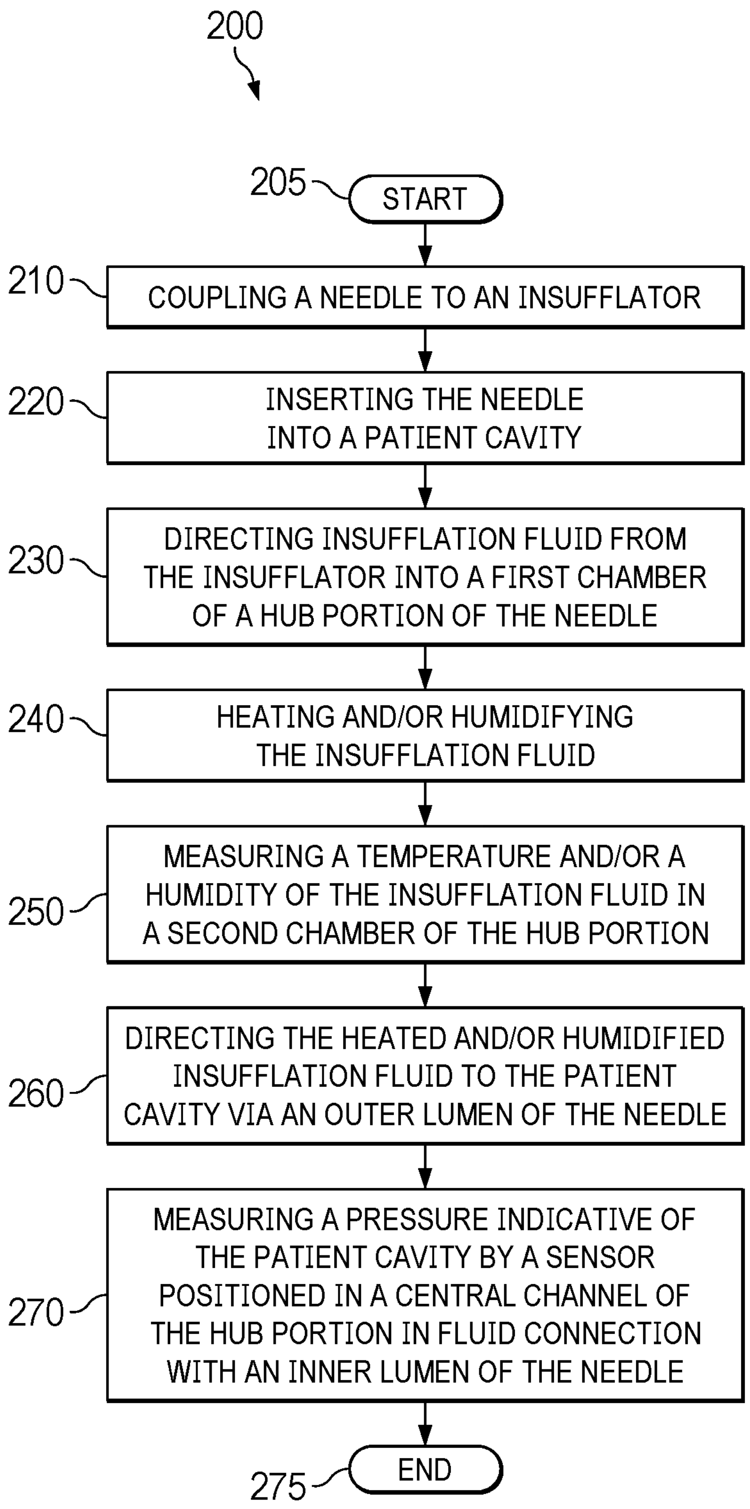
FIG. 2 is a flow chart illustrating a method of insufflating a body cavity using the insufflation needle depicted in FIGS. 1A and 1B, according to certain embodiments of the present invention.

FIG. 1A depicts a cross section of a particular embodiment of an insufflation needle configured to deliver insufflation fluid to a body cavity at flow rates sufficient to maintain pneumoperitoneum for the duration of surgery. FIG. 1B is a perspective view of the insufflation needle of FIG. 1A. FIG. 2 illustrates a method for insufflating a body cavity, e.g., using the insufflation needle illustrated in FIGS. 1A and 1B.

FIG. 1A shows a needle 100 configured to deliver insufflation fluid to a body cavity at flow rates greater than those achieved by conventional veress needles. Needle 100 includes a hub portion 105 and a shaft portion 110, with shaft portion 110 extending at least partially into hub portion 105. Hub portion 105 includes an upper chamber 105*a* and a bottom chamber 105*b*. In some embodiments, hub portion 105 includes a media heating pack 135 configured to heat and/or humidify insufflation fluid flowing through needle 100. As depicted in FIG. 1A, media heating pack 135 may be positioned about a central channel 130 of needle 100. In certain embodiments, media heating pack 135 includes an absorbent material (e.g., cellulose) and one or more heating coils 137 that may be concentrically arranged within media heating pack 135. Saline tubing line 155, depicted in FIG. 1B as being positioned along hub portion 105 adjacent to gas inlet 145, may provide saline solution to needle 100 to facilitate humidification of insufflation fluid flowing through needle 100. In some embodiments, electrical conduits such as wiring provided via electrical port 150 provide sufficient contacts to enable the operation of one or more of media heating pack 135 and sensors 140. As depicted in FIGS. 1A and 1B, electrical port 150 may be positioned along hub portion 105 near one or more of gas inlet 145 and saline tubing line 155.

Shaft portion 110 of needle 100 includes an outer lumen 115 circumscribing an inner lumen 120. In some embodiments of the invention, shaft portion 110 includes a plurality (i.e., two or more) of inner lumens 120. Embodiments with a plurality of inner lumens 120 may be associated with certain advantages, such as providing additional pathways to central canal 130 in the event that one inner lumen 120 is blocked or otherwise obstructed due to, e.g., skin tissue. Outer lumen 115 includes at least one aperture 117*a* positioned at a first end of outer lumen 115 and at least one aperture 117*b* positioned at a second end of outer lumen 115. As depicted in FIGS. 1A and 1B, the first end of outer lumen 115 is positioned proximal to hub portion 105 of needle 100 and the second end of outer lumen 115 terminates in a needle point 160.

In some embodiments, outer lumen 115 has a diameter between approximately 3.0 mm and 5.0 mm and a wall thickness between approximately 0.006 inches and 0.010 inches. In a preferred embodiment, outer lumen 115 has a diameter between approximately 4.3 mm and 4.8 mm and has a wall thickness between approximately 0.008 inches and 0.010 inches. As one of ordinary skill in the art will understand, outer lumen 115 contemplated by the present disclosure is larger than conventional veress needles used during initial stage insufflation that have a diameter between approximately 2.1 mm and 3.5 mm. For the avoidance of doubt, the term “approximately” is used herein to refer to +/−10%.

In contrast, inner lumen 120 has, in some embodiments, a diameter between approximately 0.8 mm and 2.0 mm and a wall thickness between approximately 0.004 inches and 0.008 inches. In a preferred embodiment, inner lumen 120 has a diameter between approximately 0.8 mm and 1.3 mm and has a wall thickness between approximately 0.006 inches and 0.008 inches.

According to the teachings of the present invention, the dimensioning of both outer lumen 115 and inner lumen 120 are fundamental to facilitating a minimal flow rate needed to maintain pneumoperitoneum during the duration of surgery, which one of ordinary skill in the art will recognize to be at least 10 liters per minute. In some particular embodiments described herein, needle 100 is configured to deliver insufflation fluid to a body cavity at a rate of between approximately 15 liters per minute to approximately 45 liters per minute. The insufflation fluid may be any suitable fluid used for insufflation purposes (e.g., carbon dioxide, nitrous oxide, helium, argon).

Outer lumen 115 and inner lumen 120 may be comprised of any suitable material. For example, either or both of outer lumen 115 and inner lumen 120 may be comprised of stainless steel, carbon fiber, and/or biocompatible plastics. Selection of a suitable material for outer lumen 115 and/or inner lumen 120 may consider, inter alia, wall thickness, as materials that are too thick would impede or otherwise restrict the fluid flow paths and hinder, e.g., insufflation fluid from being delivered to the body cavity at rates exceeding 10 liters per minute. In certain embodiments, the wall thickness of outer lumen 115 and inner lumen 120 is approximately 0.000125 inches.

Needle 100 may optionally include a bobbin 125 positioned within the second end of outer lumen 115. Bobbin 125 is configured to move from a first position to a second position, the first position being more distal to hub portion 105 than the second position. In some embodiments, bobbin 125 is configured to move from the first position to the second position and vice versa due to inclusion of, e.g., a spring 132 located within central channel 130. Bobbin 125 may include one or more apertures 127 that provide a fluid flow path to inner lumen 120 and, in turn, to central channel 130, as depicted in FIG. 1A.

In the first position (depicted in FIG. 1A), bobbin 125 serves as a protective element to needle point 160 and does not block or otherwise obstruct the opening provided by apertures positioned at the second end of outer lumen 115, for example, aperture(s) 117*b*. As will be discussed in detail with respect to FIG. 2, insufflation fluid flowing through needle 100 will be directed through hub 105 and into outer lumen 115, before being directed into the body cavity through aperture(s) 117*b*. In the second position (depicted in FIG. 1B), bobbin 125 moves proximally toward hub 105, resulting in exposure of needle point 160 and blockage or obstruction of the opening provided by apertures positioned at the second end of outer lumen 115, for example, aperture(s) 117*b*. In such position, insufflation fluid is restricted from flowing through aperture(s) 117*b* and into the body cavity. As one of ordinary skill in the art will recognize, needle point 160 is configured to pierce the skin of a patient, thereby facilitating insertion of needle 100 into the body cavity, and includes an aperture that terminates radially.

FIG. 1A also illustrates one or more sensors 140 positioned within hub portion 105. As depicted, needle 100 includes a first sensor 140*a* positioned within central channel 130 of hub portion 105 and a second sensor 140*b* positioned within bottom chamber 105*b*. Sensors 140 may be configured to measure any desirable environmental factor(s) including, for example, temperature, humidity, and pressure. In some embodiments, sensor 140*a* is configured to provide an indication of a pressure in the body cavity and sensor 140*b* is configured to provide an indication of the heat and/or humidity of the insufflation fluid flowing through bottom chamber 105*b*. Although this disclosure describes and depicts needle 100 as including only sensors 140*a* and 140*b*, this disclosure specifically recognizes that needle 100 may include any desirable number of sensors, such as one or more backup pressure sensors positioned in central channel 130 and one or more additional temperature and/or humidity sensors positioned within hub 105.

As is also depicted in FIGS. 1A and 1*s* additionally depicted in FIG. 1B, needle 100 may also include gas inlet 145, which forms part of the insufflation fluid pathway to the body cavity. In some embodiments, a conduit couples needle 100 to an insufflator (e.g., an insufflator described in U.S. Pat. No. 11,541,191, which is incorporated by reference) via gas inlet 145. The conduit may be any conduit suitable for delivering insufflation fluid to needle 100. As an example, such conduit may be formed of or otherwise comprise flexible PVC tubing. As shown in FIGS. 1A and 1B, gas inlet 145 may be positioned along the outside of hub portion 105 and provide a fluid flow pathway to upper chamber 105*a* of needle 100. In some embodiments, insufflation fluid is heated and/or humidified before being directed to needle 100. In other embodiments, insufflation fluid is heated and/or humidified after reaching needle 100, for example by passing through media heating pack 135. As previously discussed, one or more sensors 140 (e.g., pressure and/or temperature sensors) may be positioned within hub 105, in one or more of upper chamber 105*a* and bottom chamber 105*b*.

In some embodiments of the present invention, insufflation fluid is delivered from an insufflator to needle 100 through a conduit coupled to gas inlet 145. The insufflation fluid is thereafter delivered to upper chamber 105*a* before it is directed across media heating pack 135 for heating and/or humidification. As will be recognized by one of ordinary skill in the art, insufflation fluid should be heated to approximately between 70-99° F. and have a relative humidity of approximately between 70-100% when delivered to the body cavity. The heated and/or humidified insufflation fluid is then directed into lower chamber 105*b*. As discussed above, lower chamber 105*b* may include one or more sensors, e.g., sensor 140*b*, configured to measure, e.g., the pressure, humidity, and/or temperature of the insufflation fluid upon reaching bottom chamber 105*b*. The heated and/or humidified insufflation fluid may then be directed through one or more apertures 117*a* into the first end of outer lumen 115. The heated and/or humidified insufflation fluid then moves distally through outer lumen 115 and is directed into the body cavity through one or more apertures 117*b*.

As one of ordinary skill in the art will recognize, it is advantageous to monitor, continuously and/or intermittently, the pressure of the body cavity during surgery to ensure that it is being appropriately insufflated. One or more sensors 140, such as sensor 140*a*, is positioned in direct fluid contact with body cavity via inner lumen 120, when bobbin 125 is in the first position (see FIG. 1A). In particular, as described above, aperture(s) 127 in bobbin 125 provides direct fluid contact between the body cavity and inner lumen 120 when bobbin 125 is in the first position.

As discussed above, FIG. 1B illustrates a perspective view of needle 100 with bobbin 125 in the second position. In this position, needle 100 is configured to pierce the skin of a patient with needle point 160, thereby facilitating insertion of needle 100 into the body cavity in preparation of insufflation. As is also discussed above, bobbin 125 prevents insufflation fluid from entering the body cavity when bobbin 125 is in the second position because bobbin 125 blocks or otherwise obstructs the opening(s) formed by aperture(s) 117*b* at the second end of outer lumen 115. The blocking or obstruction of the opening(s) formed by aperture(s) 117*b* is advantageous because it inhibits such opening(s) from being obstructed or clogged with organic tissue, such as skin tissue.

Upon penetration of the patient's skin and insertion of needle 100 into the body cavity, bobbin 125 may return to the first position (see FIG. 1A), where the bobbin provides a protective element to needle point 160. As one of ordinary skill in the art will recognize, having bobbin 125 extend beyond needle point 160 reduces the risk of accidentally piercing or puncturing an organ while insufflating with needle 100. In the first position, openings formed by aperture(s) 117*b* are exposed such that heated and/or insufflation fluid can flow from outer lumen 115 into the body cavity. Additionally, in the first position, aperture(s) 127 in bobbin 125 provide a fluid flow pathway from the body cavity to inner lumen 120 and further to central channel 130.

FIG. 2 is a flowchart illustrating a method of insufflating a body cavity using needle 100. The method 200 begins at a step 205 and proceeds to a step 210. At step 210, needle 100 is coupled to an insufflator. In some embodiments, needle 100 may be coupled to an insufflator via a conduit, such as the conduit described above. The coupling of needle 100 to an insufflator enables insufflation fluid to be directed from the insufflator to needle 100. After coupling needle 100 to an insufflator, method 200 may proceed to a step 220.

At step 220, needle 100 is inserted into a body cavity. As described herein, insertion of needle 100 into the body cavity may include piercing the patient's skin with needle point 160, which becomes exposed when bobbin 125 moves from a first position to a second position. Upon entry of needle 100 into the body cavity, bobbin 125 may return to the first position. In some embodiments, the method then proceeds to a step 230.

At step 230, insufflation fluid is directed from the insufflator into first chamber (e.g., upper chamber 105*a*) of a hub portion 105 of needle 100. As described above, insufflation fluid may be carried from the insufflator to needle 100 via a conduit, such as flexible PVC tubing, that may couple to needle 100 at gas inlet 145. Gas inlet 145 may, in some embodiments, direct the insufflation fluid to first chamber 105*a*. In some embodiments, after directing the insufflation fluid to first chamber 105*a*, method 200 proceeds to a step 240.

At step 240, the insufflation fluid is heated and/or humidified. In certain embodiments, the insufflation fluid is heated and/or humidified by media heating pack 135. As discussed above, media heating pack 135 may be formed of an absorbent material and may include a concentric arrangement of one or more heating coils 137 that may be powered by electrical conduits fed through electrical port 150. As is also discussed above, media heating pack may humidify the insufflation fluid using saline that is directed to needle 100 via saline tubing line 155. Media heating pack 135 may be positioned within hub portion 105 of needle 100 and be configured to heat and/or humidify the insufflation fluid as it is directed from upper chamber 105*a* to bottom chamber 105*b* through media heating pack 135. After heating and/or humidifying the insufflation fluid, method 200 may proceed to an optional step 250.

At optional step 250, a temperature and/or humidity of the insufflation fluid in the second chamber (e.g., bottom chamber 105*b*) of hub portion 105 is measured. In some embodiments, the temperature and/or humidity of the insufflation fluid is measured by one or more sensors (e.g., sensor(s) 140*b*) positioned within bottom chamber 105*b*. As one of ordinary skill in the art will recognize, there are advantages to delivering sufficiently heated and humidified insufflation fluid to a body cavity. After measuring the temperature and/or humidity of the insufflation fluid, method 200 may proceed to a step 260.

At step 260, the heated and/or humidified insufflation fluid is directed to the body cavity via outer lumen 115 of needle 100. Outer lumen 115 is dimensioned to facilitate the flow of insufflation fluid at rates exceeding 10 liters per minute. In some embodiments, outer lumen 115 has a diameter between approximately 3.0 mm and 5.0 mm and a wall thickness between approximately 0.006 inches and 0.010 inches. As described and depicted herein, outer lumen 115 circumscribe one or more inner lumens 120 that are also dimensioned to ensure that insufflation fluid may flow at rates exceeding 10 liters per minute. In some embodiments, the heated and/or humidified insufflation fluid is directed to the body cavity via aperture(s) 117*b* in outer lumen 115 positioned proximal to needle point 160. After directing the heated and/or humidified insufflation fluid to the body cavity, method 200 may proceed to a step 270.

At step 270, a pressure indicative of the body cavity is measured by a sensor (e.g., sensor 140*a*) positioned in central channel 130 of hub portion 105 in fluid connection with inner lumen 120 of needle 100. As will be recognized by one of ordinary skill in the art, such pressure measurement may be used to adjust the flow rate of the insufflation fluid to ensure pneumoperitoneum is maintained in the body cavity during surgery. After measuring a pressure indicative of the body cavity, method 200 may proceed to an end step 275.

For the avoidance of doubt, the above steps may be performed in any desired order and may not necessarily be performed sequentially.

Although FIGS. 1A through 2 have been described above as including particular steps and/or components, the method and systems of these FIGS. may include any combination of any of the described steps and/or components and any of the options or features described herein, as would be understood by one of ordinary skill in the art. For example, any of the steps, options, or features described herein may be utilized in combination with the illustrated embodiments of FIGS. 1A through 2 and/or any number of the other steps, options, or features also described herein, as would be understood by one of ordinary skill in the art.

Modifications, additions, or omissions may be made to the systems, apparatuses, and methods described herein without departing from the scope of the disclosure. The components of the systems and apparatuses may be integrated or separated. Moreover, the operations of the systems and apparatuses may be performed by more, fewer, or other components. One skilled in the art will also understand that the system contemplated by this disclosure can include other components that are not illustrated but are typically included with such systems. Additionally, operations of the systems and apparatuses may be performed using any suitable logic comprising software, hardware, and/or other logic. As used in this document, "each" refers to each member of a set or each member of a subset of a set.

Although this disclosure has been described in terms of certain embodiments, alterations and permutations of the embodiments will be apparent to those skilled in the art. Accordingly, the above description of the embodiments does not constrain this disclosure. Other changes, substitutions, and alterations are possible without departing from the spirit and scope of this disclosure.

What is claimed is:

1. A system comprising:
- an insufflator configured to supply insufflation fluid; and
- a needle coupled to the insufflator and configured to facilitate delivery of the insufflation fluid to a body cavity, the needle comprising a shaft portion extending at least partially into a hub portion, wherein:
  - the shaft portion comprises an outer lumen and at least one inner lumen;
  - the outer lumen:
    - has a diameter between approximately 3.0 mm and 5.0 mm; and
    - comprises at least one aperture at a first end of the outer lumen and at least one aperture at a second end of the outer lumen, wherein the first end is positioned proximal to the hub portion of the needle and the second end terminates in a needle point;
  - the at least one inner lumen:
    - has a diameter between approximately 0.8 mm and 2.0 mm; and
  - a spring-loaded bobbin positioned within the second end of the outer lumen and configured to move from a first position to a second position, wherein:
    - the first position allows the insufflation fluid to flow through the at least one aperture at the second end of the outer lumen; and
    - the second position exposes the needle point of the outer lumen and prevents the insufflation fluid from flowing through the at least one aperture at the second end of the outer lumen.

2. The system of claim 1, wherein the system is configured to deliver the insufflation fluid to the body cavity at a rate exceeding 10 liters per minute.

3. The system of claim 2, wherein the system is configured to deliver the insufflation fluid to the body cavity at a rate of approximately 15 to 45 liters per minute.

4. The system of claim 1, wherein the needle further comprises at least one pressure sensor configured to provide an indication of a pressure in the body cavity, the at least one pressure sensor being positioned within a central channel of the hub portion, the central channel being in fluid connection with the at least one inner lumen.

5. The system of claim 1, wherein the needle further comprises at least one temperature sensor positioned in the hub portion of the needle, the at least one temperature sensor configured to provide an indication of a temperature of the insufflation fluid.

6. The system of claim 1, wherein the needle further comprises a media heating pack configured to heat and humidify the insufflation fluid, the media heating pack positioned within the hub portion of the needle about a central channel.

7. The system of claim 6, wherein the insufflation fluid is directed into a lower chamber of the hub portion after passing through the media heating pack before being directed into the at least one aperture at the first end of the outer lumen.

8. The system of claim 1, wherein the spring-loaded bobbin comprises at least one aperture in fluid connection with the at least one inner lumen.

9. The system of claim 1, wherein one or more of the outer lumen or the at least one inner lumen are comprised of a first material, the first material being selected from the group consisting of: stainless steel, carbon fiber, and biocompatible plastics.

10. An insufflation needle comprising:
- a hub portion; and
- a shaft portion extending at least partially into the hub portion, the shaft portion comprising an outer lumen and at least one inner lumen, wherein:
  - the outer lumen has a diameter between approximately 3.0 mm and 5.0 mm and comprises at least one aperture at a first end of the outer lumen and at least one aperture at a second end of the outer lumen, the first end being positioned proximal to the hub portion of the needle and the second end terminating in a needle point;
  - the at least one inner lumen has a diameter between approximately 0.8 mm and 2 mm; and
- a spring-loaded bobbin positioned within the second end of the outer lumen and configured to move from a first position to a second position, wherein:
  - the first position allows the insufflation fluid to flow through the at least one aperture at the second end of the outer lumen; and
  - the second position exposes the needle point of the outer lumen and prevents the insufflation fluid from flowing through the at least one aperture at the second end of the outer lumen.

11. The insufflation needle of claim 10, wherein the insufflation needle is configured to deliver insufflation fluid to a body cavity at a rate exceeding 10 liters per minute.

12. The insufflation needle of claim 11, wherein the insufflation needle is configured to deliver insufflation fluid to a body cavity at a rate of approximately 15 to 45 liters per minute.

13. The insufflation needle of claim 10, further comprising at least one pressure sensor configured to provide an indication of a pressure in the body cavity, the at least one pressure sensor being positioned within a central channel of the hub portion, the central channel being in fluid connection with the at least one inner lumen.

14. The insufflation needle of claim 10, further comprising at least one temperature sensor positioned in the hub portion, the at least one temperature sensor configured to provide an indication of a temperature of an insufflation fluid.

15. The insufflation needle of claim 10, further comprising a media heating pack configured to heat and/or humidify an insufflation fluid, the media heating pack being positioned within the hub portion about a central channel.

16. The insufflation needle of claim 15, wherein the hub portion comprises an upper chamber and a lower chamber, the lower chamber facilitating access to the at least one aperture at the first end of the outer lumen.

17. The system of claim 10, wherein the spring-loaded bobbin comprises at least one aperture in fluid connection with the at least one inner lumen.

18. The system of claim 10, wherein one or more of the outer lumen or the at least one inner lumen are comprised of a first material, the first material being selected from the group consisting of: stainless steel, carbon fiber, and biocompatible plastics.

* * * * *